United States Patent
Hill

(10) Patent No.: US 7,064,838 B2
(45) Date of Patent: Jun. 20, 2006

(54) APPARATUS AND METHOD FOR MEASUREMENT OF FIELDS OF BACKSCATTERED AND FORWARD SCATTERED/REFLECTED BEAMS BY AN OBJECT IN INTERFEROMETRY

(75) Inventor: Henry Allen Hill, Tucson, AZ (US)

(73) Assignee: Zetetic Institute, Tucson, AZ (US)

( * ) Notice: Subject to any disclaimer, the term of this patent is extended or adjusted under 35 U.S.C. 154(b) by 68 days.

(21) Appl. No.: 10/816,172

(22) Filed: Apr. 1, 2004

(65) Prior Publication Data

US 2004/0227950 A1 Nov. 18, 2004

Related U.S. Application Data

(60) Provisional application No. 60/460,129, filed on Apr. 3, 2003.

(51) Int. Cl.
*G01B 9/02* (2006.01)

(52) U.S. Cl. .................................................. 356/450
(58) Field of Classification Search ................. 356/450
See application file for complete search history.

(56) References Cited

U.S. PATENT DOCUMENTS

| | | |
|---|---|---|
| 3,628,027 A | 12/1971 | Brauss |
| 3,748,015 A | 7/1973 | Offner |
| 4,011,011 A | 3/1977 | Hemstreet et al. |
| 4,226,501 A | 10/1980 | Shafer |
| 4,272,684 A | 6/1981 | Seachman |
| 4,685,803 A | 8/1987 | Sommargren |
| 4,733,967 A | 3/1988 | Sommargren |
| 5,220,403 A | 6/1993 | Batchelder |
| 5,241,423 A | 8/1993 | Chiu et al. |
| 5,327,223 A | 7/1994 | Korth |
| 5,485,317 A | 1/1996 | Perissinotto |
| 5,602,643 A | 2/1997 | Barrett |
| 5,614,763 A | 3/1997 | Womack |
| 5,633,972 A | 5/1997 | Walt |
| 5,659,420 A | 8/1997 | Wakai |
| 5,699,201 A | 12/1997 | Lee |
| 5,760,901 A | 6/1998 | Hill |
| 5,828,455 A | 10/1998 | Smith |

(Continued)

OTHER PUBLICATIONS

U.S. Appl. No. 09/852,369, filed Jan. 3, 2002, Hill.

(Continued)

*Primary Examiner*—Gregory J. Toatley, Jr.
*Assistant Examiner*—Denise B Anderson
(74) *Attorney, Agent, or Firm*—Wilmer Cutler Pickering Hale and Dorr LLP

(57) ABSTRACT

An interferometry system including an interferometer that includes a source imaging system that focuses an input beam onto a spot on or in the object and an object imaging system that images the spot onto a detector element as an interference beam, wherein the source imaging system is characterized by a first aperture stop that defines a first aperture and includes a first phase shifter that introduces a first phase shift in light passing through a first region of the first aperture relative to light passing through a second region of the first aperture, and wherein the object imaging system is characterized by a second aperture stop that defines a second aperture and includes a second phase shifter that introduces a second phase shift in light passing through a first region of the second aperture relative to light passing through a second region of the second aperture.

47 Claims, 4 Drawing Sheets

U.S. PATENT DOCUMENTS

| | | |
|---|---|---|
| 5,894,195 A | 4/1999 | McDermott |
| 5,915,048 A | 6/1999 | Hill et al. |
| 6,052,231 A | 4/2000 | Rosenbluth |
| 6,091,496 A | 7/2000 | Hill |
| 6,124,931 A | 9/2000 | Hill |
| 6,271,923 B1 | 8/2001 | Hill |
| 6,330,065 B1 | 12/2001 | Hill |
| 6,445,453 B1* | 9/2002 | Hill ............................ 356/450 |
| 6,447,122 B1 | 9/2002 | Kobayashi et al. |
| 6,480,285 B1 | 11/2002 | Hill |
| 6,552,805 B1 | 4/2003 | Hill |
| 6,552,852 B1 | 4/2003 | Hill |
| 6,597,721 B1 | 7/2003 | Hutchinson et al. |
| 6,606,159 B1 | 8/2003 | Hill |
| 6,667,809 B1* | 12/2003 | Hill ............................ 356/511 |
| 6,714,349 B1 | 3/2004 | Nam |
| 6,717,736 B1 | 4/2004 | Hill |
| 6,753,968 B1 | 6/2004 | Hill |
| 6,775,009 B1 | 8/2004 | Hill |
| 6,847,029 B1 | 1/2005 | Hill |
| 6,847,452 B1 | 1/2005 | Hill |
| 2002/0074493 A1 | 6/2002 | Hill |
| 2003/0174992 A1 | 9/2003 | Levene |
| 2004/0201852 A1 | 10/2004 | Hill |
| 2004/0201853 A1 | 10/2004 | Hill |
| 2004/0201854 A1 | 10/2004 | Hill |
| 2004/0201855 A1 | 10/2004 | Hill |
| 2004/0202426 A1 | 10/2004 | Hill |
| 2004/0227950 A1 | 11/2004 | Hill |
| 2004/0227951 A1 | 11/2004 | Hill |
| 2004/0228008 A1 | 11/2004 | Hill |
| 2004/0246486 A1 | 12/2004 | Hill |
| 2004/0257577 A1 | 12/2004 | Hill |

OTHER PUBLICATIONS

U.S. Appl. No. 09/917,402, filed Jul. 27, 2001, Hill.
U.S. Appl. No. 10/765,368, filed Jan. 27, 2004, Hill.
U.S. Appl. No. 60/442,858, filed Jan. 2003, Hill.
U.S. Appl. No. 60/442,982, filed Jan. 29, 2003, Hill.
U.S. Appl. No. 60/444,707, filed Feb. 4, 2003, Hill.
U.S. Appl. No. 60/445,739, filed Feb. 7, 2003, Hill.
U.S. Appl. No. 60/447,254, filed Feb. 13, 2003, Hill.
U.S. Appl. No. 60/459,425, filed Apr. 11, 2003, Hill.
U.S. Appl. No. 60/460,129, filed Apr. 3, 2003, Hill.
Silfvast, W. (1995) "Lasers", *Handbook of Optics,* New York:: McGraw-Hill, Ch. 11.
Stoicheff, et al. "Tunable, Coherent Sources for High Resolution VUV and XUV Spectroscopy", *Laser Techniques for Extreme Ultraviolet Spectroscopy,* p. 19 (1982).
Harris, et al. "Generation of Ultraviolet and Vacuum Ultraviolet Radiation" *Laser Spectroscopy*.
Kung, A.H., "Generation of Tunable Picosecond VUV Radiation" *Appl. Phys Lett.* 25, p. 653 (1974).
D'ariano, et al. "Lower Bounds on Phase Sensitivity in Ideal and Feasible Measurements" *Phys. Rev. A* 49, pp. 3022-3036 (1994).

* cited by examiner

APPARATUS AND METHOD FOR MEASUREMENT OF FIELDS OF BACKSCATTERED AND FORWARD SCATTERED/REFLECTED BEAMS BY AN OBJECT IN INTERFEROMETRY

This application also claims the benefit of U.S. Provisional Application No. 60/460,129, filed Apr. 3, 2003.

TECHNICAL FIELD

This invention relates to the imaging of spots in or on a substrate using interferometry.

BACKGROUND OF THE INVENTION

The prior art teaches the practice of measuring the amplitudes of fields of forward scattered/reflected beams by an object as a function of angle of incidence in ellipsometric measurements. The prior art does not, however, teach backscattered imaging of an object by measuring amplitudes of fields of backscattered beams by an object using either interferometric non-ellipsometric or in interferometric ellipsometric measurements. Nor does it teach backscattered imaging involving joint measurements of conjugated quadratures of fields of backscattered beams by an object using either interferometric non-ellipsometric or in interferometric ellipsometric measurements.

The prior art also teaches the practice of measuring the amplitudes of fields of forward scattered/reflected beams by an object as a function of angle of incidence in ellipsometric measurements for a single spot on a substrate or for a small number of spots on a substrate. It does not, however, teach the practice of backscattered imaging or of measuring the amplitudes of fields of forward scattered/reflected beams by spots in or on a substrate by measuring simultaneously the amplitudes of fields of the backscattered beams or of the forward scattered/reflected beams by an array of a large number of spots in or on an object in either non-interferometric or in interferometric ellipsometric measurements. Nor does it teach the practice of backscattered imaging or of measuring the amplitudes of fields of forward scattered/reflected beams by spots in or on a substrate with simultaneous joint measurements of conjugated quadratures of fields of the backscattered beams or of the forward scattered/reflected beams by a large array of spots in or on an object in interferometric ellipsometric or non-ellipsometric measurements.

SUMMARY OF THE INVENTION

Embodiments of the invention that are described herein generate one-dimensional, two-dimensional, and three-dimensional backscattered images of an object with the measurement of amplitudes of fields of backscattered beams by an object in interferometric non-ellipsometric and in interferometric ellipsometric measurements. Certain embodiments further generate one-dimensional, two-dimensional, and three-dimensional backscattered images of an object with joint measurements of conjugated quadratures of fields of backscattered beams by an object in either interferometric non-ellipsometric or in interferometric ellipsometric measurements.

In other embodiments, backscattered images of an object are generated with simultaneous measurements made of amplitudes of fields of backscattered beams by an array of a large number of spots in or on an object in either interferometric non-ellipsometric or in interferometric ellipsometric measurements. In yet other embodiments, backscattered images of an object are generated with simultaneous measurements made of joint measurements of conjugated quadratures of fields of backscattered beams by a large array of spots in or on an object in either interferometric non-ellipsometric or in interferometric ellipsometric measurements. As will become apparent, many of the embodiments described herein may also be used in forward scattered/reflection imaging of spots in or on a substrate.

In general, in one aspect, the invention features an interferometry system for making interferometric measurements of an object. The system includes a source assembly that generates an input beam; a detector assembly that includes a detector element; and an interferometer that includes a source imaging system that images the input beam onto a spot on or in the object and an object imaging system that images the spot onto the detector element as an interference beam, wherein the object imaging system combines light coming from the spot with a reference beam to produce the interference beam. The source imaging system is characterized by a first aperture stop that defines a first aperture and includes a first phase shifter that introduces a first phase shift in light passing through a first region of the first aperture relative to light passing through a second region of the first aperture, wherein the second region of the first aperture being the region of the aperture that is outside of the first region of the first aperture. The object imaging system is characterized by a second aperture stop that defines a second aperture and includes a second phase shifter that introduces a second phase shift in light passing through a first region of the second aperture relative to light passing through a second region of the second aperture, wherein the second region of the second aperture being the region of the aperture that is outside of the first region of the second aperture.

Other embodiments include one or more of the following features. The first and second phase shifters are oriented relative to each other such that any component of the input beam that reaches the detector element as a result of being forward scattered/reflected by the object passes through only one of the first and second phase shifters when traversing from the source assembly to the detector element. In addition, the first and second phase shifters are oriented relative to each other such that any component of the input beam that reaches the detector element as a result of being backscattered by the object passes through either both the first and second phase shifters or through neither of the first and second phase shifters when traversing from the source assembly to the detector element. The first phase shift is $\pi/2$ and the second phase shift is $\pi/2$. The first region of the first aperture occupies one half of the area of the first aperture and the first region of the second aperture occupies one half of the area of the second aperture. The first and second regions of the first aperture are of equal area and the first and second regions of the second aperture are of equal area.

Still other embodiments include one or more of the following features. The object imaging system includes a first imaging system, a mask defining a pinhole, and a second imaging system, wherein the first imaging system images the spot on the pinhole of the mask and the second imaging system images the pinhole of the mask onto the detector element. The second phase shifter is located in the first imaging system. The first imaging system and the source imaging system are both implemented by the same imaging system. The second imaging system images the pinhole onto the detector element. The first phase shifter is a thin optical film on a portion of a surface of an optical element within the source imaging system and the second phase shifter is also implemented by that same thin film. The interferometer includes a catadioptric imaging system that implements both the source imaging system and the first imaging system. The catadioptric imaging system includes a first catadioptric element, a second catadioptric element, and a beam splitter between the first and second catadioptric elements. The source assembly includes a pulsed or shuttered source for generating the input beam. The interferometry system may be an interferometric microscopy system, a interferometric confocal microscopy system, or an interferometric ellipsometric microscopy system, to name only a few possibilities.

In general, in another aspect, the invention features an interferometry system for making interferometric measurements of an object. The system includes: a source assembly that generates an array of input beams; a detector assembly that includes an array of detector elements; and an interferometer that includes a source imaging system that images the array of input beams onto an array of spots on or in the object and an object imaging system that images the array of spots onto the array of detector elements as an array of interference beams, wherein the object imaging system combines light coming from each spot of the array of spots with a corresponding reference beam to produce a corresponding interference beam of the array of interference beams. The source imaging system is characterized by a first aperture stop that defines a first aperture and includes a first phase shifter that introduces a first phase shift in light passing through a first region of the first aperture relative to light passing through a second region of the first aperture, wherein the second region of the first aperture is the region of the aperture that is outside of the first region of the first aperture. The object imaging system is characterized by a second aperture stop that defines a second aperture and includes a second phase shifter that introduces a second phase shift in light passing through a first region of the second aperture relative to light passing through a second region of the second aperture, wherein the second region of the second aperture being the region of the aperture that is outside of the first region of the second aperture.

Other embodiments include one or more of the following features. The first and second phase shifters are oriented relative to each other such that any component of the array of input beams that reaches the detector element as a result of being forward scattered/reflected by the object passes through only one of the first and second phase shifters when traversing from the source assembly to the detector element. In addition, the first and second phase shifters are oriented relative to each other such that any component of the array of input beams that reaches the detector element as a result of being backscattered by the object passes through either both of the first and second phase shifters or through neither of the first and second phase shifters when traversing from the source assembly to the detector assembly. The object imaging system includes a first imaging system, a object-side mask defining an array of pinholes, and a second imaging system, wherein the first imaging system images the array of spots on the array of pinholes so that each imaged spot of the imaged array of spots is aligned with a corresponding different one of the pinholes of the array of pinholes and wherein the second imaging system images the array of pinholes onto the array of detector elements. The interferometer includes a catadioptric imaging system that implements both the source imaging system and the first imaging system. The catadioptric imaging system includes a first catadioptric element, a second catadioptric element, and a beam splitter between the first and second catadioptric elements. The source assembly includes a source-side mask defining an array of pinholes. The detector-side mask and the source-side mask are implemented by the same mask. The source assembly includes a pulsed source for generating the array of input beams. The interferometry system also includes an object stage for holding the object, a first transducer assembly for moving the object stage so as to scan the object during operation, and a second transducer assembly for moving the detector-side mask during operation. The interferometry system further includes a controller programmed to cause the first transducer to move the object while at the same time causing the second transducer assembly to move the detector-side mask so that the detector-side mask tracks a conjugate image of the substrate during operation.

In general, in still yet another aspect, the invention features a method of making interferometric measurements of an object. The method involves: generating a input beam; deriving first and second measurement beams from the input beam; shifting the first measurement beam in phase relative to the second measurement beam by a first amount; focusing the first and second measurement beams onto a spot on or in the object to produce a first return measurement beam and a second return measurement beam, wherein the first return measurement beam results from forward reflection and/or forward scattering of the first measurement beam by the object plus backscattering of the second measurement beam by the object, and the second measurement beam results from forward reflection and/or forward scattering of the second measurement beam by the object plus backscattering of the first measurement beam by the object; shifting the second return measurement beam in phase relative to the first return measurement beam by a second amount; interfering the first and return second return measurement beams with a reference beam to produce an interference beam; and focusing the interference beam onto the detector element.

Other embodiments include one or more of the following features. The first and second amounts of phase shift are such that the backscattering portions of the first and second return measurement beams substantially cancel and the forward reflected and/or forward scattering portions of the first and second return measurement beams reinforce each other. The first and second amounts of phase shift are equal to $\pi/2$.

An advantage of at least one embodiment is that one-dimensional, two-dimensional, and three-dimensional backscattered images of an object are generated with the measurement of amplitudes of fields of beams backscattered by an object in interferometric non-ellipsometric and in interferometric ellipsometric measurements.

Another advantage of at least one embodiment is that one-dimensional, two-dimensional, and three-dimensional backscattered images of an object are generated with joint measurements of conjugated quadratures of fields of beams backscattered by an object in either interferometric non-ellipsometric or in interferometric ellipsometric measurements.

An advantage of at least one embodiment is that backscattered images of an object are generated with simultaneous measurements of amplitudes of fields of beams backscattered by an array of a large number of spots in or on an object in either interferometric non-ellipsometric or in interferometric ellipsometric measurements.

An advantage of at least one embodiment is that backscattered images of an object are generated with simultaneous measurements of joint measurements of conjugated quadratures of fields of beams backscattered by a large array of spots in or on an object in either interferometric non-ellipsometric or in interferometric ellipsometric measurements.

Another advantage of at least one embodiment is that either bi- or quad-homodyne detection methods can be used in non-ellipsometric measurements to obtain joint measurements of conjugated quadratures of fields of beams reflected/scattered by a substrate being imaged.

Another advantage of at least one embodiment is that either a variant of the bi- or quad-homodyne detection method can be used in ellipsometric measurements to obtain joint measurements of conjugated quadratures of fields of beams reflected/scattered by a substrate being imaged.

Another advantage of at least one embodiment is that relative phase shifts between the arrays of reference and measurement beams can be introduced by changing the frequencies of components of an input beam.

Another advantage of at least one embodiment is backscattered imaging of a substrate with a lateral resolution of the order of microns may be obtained with a working distance of the order of a mm for ellipsometric measurements.

Another advantage of at least one embodiment is backscattered imaging of an interior portion of a substrate with a lateral resolution of the order of microns may be obtained with a working distance of the order of a mm for ellipsometric measurements.

Another advantage of at least one embodiment is that in certain embodiments, the phases of components of an input beam do not affect measured conjugated quadratures of fields.

For each of the advantages with respect to backscattered imaging, there are corresponding advantages with respect to forward scattered/reflection imaging of a substrate.

DETAILED DESCRIPTION

Several embodiments are described that comprise interferometric confocal and non-confocal ellipsometric and non-ellipsometric microscopy systems. A general description of embodiments incorporating the present invention will first be given for interferometer systems wherein the single-, double-, bi-, and quad-homodyne detection methods and variants thereof are used for making measurements of conjugated quadratures of fields of either polarized beams or orthogonally polarized beams scattered/reflected by a measurement object. For those embodiments that use bi- and quad-homodyne detection methods and variants thereof, joint measurements are made of conjugated quadratures of fields of either polarized beams or orthogonally polarized beams scattered/reflected by a measurement object.

Figure 1A:
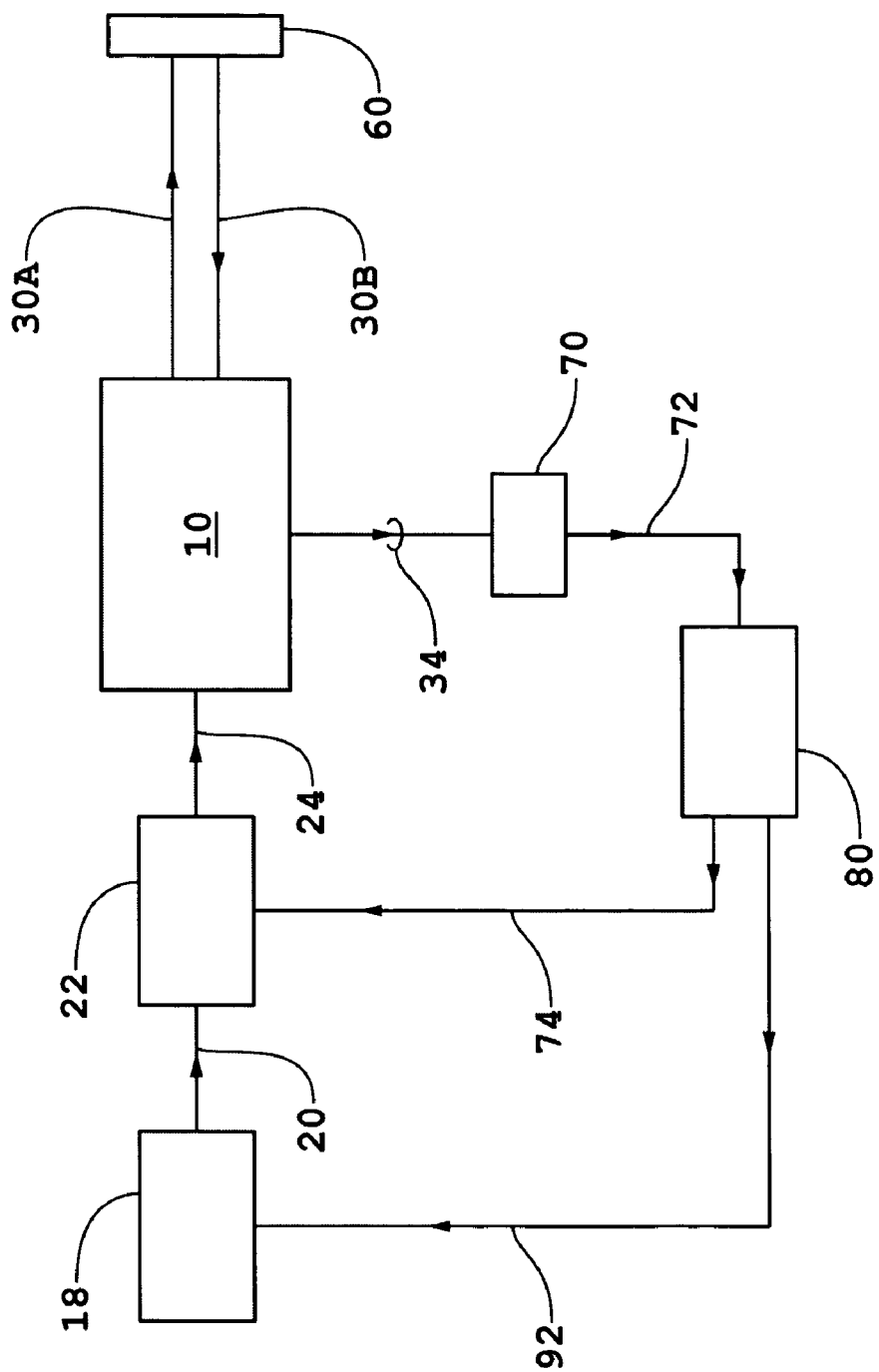
FIG. 1a is a diagram of an interferometric system that uses the single-, double-, bi-, and quad-homodyne detection methods and variants thereof.

Referring to FIG. 1a, an interferometer system is shown diagrammatically comprising an interferometer 10, a source 18, a beam-conditioner 22, detector 70, an electronic processor and controller 80, and a measurement object, substrate 60. Source 18 is a pulsed or shuttered source that generates input beam 20 comprising one or more frequency components. Beam 20 is incident on and exits beam-conditioner 22 as input beam 24 that comprises a single polarized component or two orthogonally polarized components. Each of the polarized components comprises one or more different frequency components. The measurement beam components of the frequency components of input beam 24 are coextensive in space and have the same temporal window function and the corresponding reference beam components are coextensive in space and have the same temporal window function.

Reference and measurement beams may be generated in either beam-conditioner 22 from a set of beams from source 18 or in interferometer 10 for each of the frequency components of input beam 24. Measurement beam 30A generated in either beam-conditioner 22 or in interferometer 10 is incident on substrate 60. Measurement beam 30B is a return measurement beam generated as either a portion of measurement beam 30A reflected and/scattered or transmitted by substrate 60. Return measurement beam 30B is combined with the reference beam in interferometer 10 to form output beam 34.

Output beam 34 is detected by detector 70 to generate one or more electrical interference signals per source pulse for the homodyne detection method used and transmitted as signal 72. Detector 70 may comprise an analyzer to select common polarization states of the reference and return measurement beam components of beam 34 to form a mixed beam. Alternatively, interferometer 10 may comprise an analyzer to select common polarization states of the reference and return measurement beam components such that beam 34 is a mixed beam.

In the practice, known phase shifts are introduced between the reference and measurement beam components of output beam 34 by two different techniques. In the first technique, phase shifts are introduced between corresponding reference and measurement beam components for each of the frequency components of output beam 34 as a consequence of a non-zero optical path difference between the reference and measurement beam paths in interferometer 10 and corresponding frequency shifts introduced to the frequency components of input beam 24 by beam-conditioner 22 and/or source 18 as controlled by signals 74 and 92, respectively, from electronic processor and controller 80. In the second technique, phase shifts are introduced between the reference and measurement beam components for each of the frequency components of input beam 24 by beam-conditioner 22 and/or source 18 as controlled by signals 74 and 92, respectively, from electronic processor and controller 80.

There are different ways to configure source 18 and beam-conditioner 22 to meet the input beam requirements of the different embodiments. Examples of beam-conditioners that may be used in the second technique comprise combinations of a two frequency generator and phase shifting type of beam-conditioner such as described in commonly owned U.S. Provisional Patent Application No. 60/442,858 (47) entitled "Apparatus and Method for Joint Measurements of Conjugated Quadratures of Fields of Reflected/Scattered Beams by an Object in Interferometry" and U.S. patent application Ser. No. 10/765,369, filed Jan. 27, 2004 (ZI-47) and entitled "Apparatus and Method for Joint Measurements of Conjugated Quadratures of Fields of Reflected/Scattered and Transmitted Beams by an Object in Interferometry". Other examples of beam-conditioners that may be used in the second technique comprising combinations of multiple frequency generators and phase shifting types of beam-conditioners such as described for example in commonly owned U.S. Provisional Patent Application Serial No. 60/459,425 (ZI-50) entitled "Apparatus and Method for Joint Measurement of Fields of Scattered/Reflected Orthogonally Polarized Beams by an Object in Interferometry" and U.S. patent application Ser. No. 10/816,180 filed Apr. 1, 2004 also entitled "Apparatus and Method for Joint Measurement of Fields of Scattered/Reflected Orthogonally Polarized Beams by an Object in Interferometry". The two U.S. Provisional Patent Applications and the two U.S. Patent Applications are all by Henry A. Hill and the contents of which are incorporated herein in their entirety by reference.

With a continuation of the description of different ways to configure source 18 and beam-conditioner 22 to meet the input beam requirements of different embodiments, source 18 will preferably comprise a pulsed source. There are a number of different ways for producing a pulsed source [see Chapter 11 entitled "Lasers", *Handbook of Optics*, 1, 1995 (McGraw-Hill, New York) by W. Silfvast]. Each pulse of source 18 may comprise a single pulse or a train of pulses such as generated by a mode locked Q-switched Nd:YAG laser. A single pulse train is referenced herein as a pulse. The word "pulse" and the phrase "a pulse train" are used herein interchangeably.

Source 18 may be configured in certain embodiments to generate two or more frequencies by techniques such as described in a review article entitled "Tunable, Coherent Sources For High-Resolution VUV and XUV Spectroscopy" by B. P. Stoicheff, J. R. Banic, P. Herman, W. Jamroz, P. E. LaRocque, and R. H. Lipson in *Laser Techniques for Extreme Ultraviolet Spectroscopy*, T. J. McIlrath and R. R. Freeman, Eds., (American Institute of Physics) p 19 (1982) and references therein. The techniques include for example second and third harmonic generation and parametric generation such as described in the articles entitled "Generation of Ultraviolet and Vacuum Ultraviolet Radiation" by S. E. Harris, J. F. Young, A. H. Kung, D. M. Bloom, and G. C. Bjorklund in *Laser Spectroscopy I*, R. G. Brewer and A. Mooradi, Eds. (Plenum Press, New York) p 59, (1974) and "Generation of Tunable Picosecond VUV Radiation" by A. H. Kung, *Appl. Phys. Lett.* 25, p 653 (1974). The contents of the three cited articles are herein incorporated in their entirety by reference.

The output beams from source 18 comprising two or more frequency components may be combined in beam-conditioner 22 by beam-splitters to form coextensive measurement and reference beams that are either spatially separated or coextensive as required in certain embodiments. The frequency shifting of the various components required in certain embodiments may be introduced in source 18, for example, by frequency modulation of input beams to parametric generators and the phase shifting of reference beams relative to measurement beams in beam-conditioner 22 may be achieved by phase shifters of the optical-mechanical type comprising for example prisms or mirrors and piezoelectric translators or of the electro-optical modulator type.

The general description is continued with reference to FIG. 1*a*. Input beam 24 is incident on interferometer 10 wherein reference beams and measurement beams are generated. The reference beams and measurement beams comprise one or two arrays of reference beams and one or two arrays of measurement beams, respectively, for non-ellipsometric and ellipsometric measurements, respectively, wherein the arrays may comprise arrays of one element. The arrays of measurement beams are focused on and/or in substrate 60 and arrays of return measurement beams are generated by reflection/scattering by substrate 60. The arrays of reference beams and return measurement beams are combined by a beam-splitter to form on or two arrays of output beams for non-ellipsometric or ellipsometric measurements, respectively. The arrays of output beams are mixed with respect to state of polarization either in interferometer 10 or in detector 70. The arrays of output beams are subsequently focused to spots on pixels of a multipixel detector and detected to generate the array of electrical interference signals 72.

The conjugated quadratures of fields of return measurement beams are obtained by using a single-, double-, bi-, quad-homodyne detection method or variant thereof. The bi- and quad-homodyne detection methods are described for example in cited U.S. Provisional Patent Application No. 60/442,858 (47) and U.S. patent application Ser. No. 10/765, 369, filed Jan. 27, 2004 (ZI-47) and entitled "Apparatus and Method for Joint Measurements of Conjugated Quadratures of Fields of Reflected/Scattered and Transmitted Beams by an Object in Interferometry". The variants of the bi- and quad-homodyne detection methods are described for example in cited U.S. Provisional Patent Application No. 60/459,425 (ZI-50) and U.S. Patent Application 10/816,180 filed Apr. 1, 2004 and entitled "Apparatus and Method for Joint Measurement of Fields of Scattered/Reflected Orthogonally Polarized Beams by an Object in Interferometry".

For the single-homodyne detection method, input beam 24 comprises a single frequency component and sets of four or eight measurements of the array of electrical interference signals 72 is made in non-ellipsometric or ellipsometric measurements, respectively. For each of the measurements of the array of electrical interference signals 72 in non-ellipsometric and ellipsometric measurements, known phase shifts are introduced between each reference beam component and respective return measurement beam component of output beam 34. The subsequent data processing procedure used to extract the conjugated quadratures of fields of beams reflected and/or scattered by a substrate is described for example in commonly owned U.S. Pat. No. 6,445,453 (ZI-14) entitled "Scanning Interferometric Near-Field Confocal Microscopy" by Henry A. Hill, the contents of which are incorporated herein in their entirety by reference.

The double-homodyne detection method which is applicable to non-ellipsometric measurements uses input beam 24 comprising four frequency components and four detectors to obtain measurements of electrical interference signals that are subsequently used to obtain conjugated quadratures in non-ellipsometric measurements. Each detector element of the four detector elements obtains a different one of the four electrical interference signal values with the four electrical interference signal values obtained simultaneously to compute the conjugated quadratures for a field. Each of the four electrical interference signal values contains only information relevant to one orthogonal component of the conjugated quadratures. The double-homodyne detection used herein is related to the detection methods such as described in Section IV of the article by G. M D'ariano and M G. A. Paris entitled "Lower Bounds On Phase Sensitivity In Ideal And Feasible Measurements," *Phys. Rev. A* 49, 3022–3036 (1994). Accordingly, the double-homodyne detection method does not make joint determinations of conjugated quadratures of fields wherein each electrical interference signal value contains information simultaneously about each of two orthogonal components of the conjugated quadratures.

In the adaptation of the double-homodyne detection method to ellipsometric measurements, input beam 24 comprises eight frequency components and eight detectors to obtain measurements of eight electrical interference signals that are subsequently used to obtain conjugated quadratures. Each detector element of the eight detector elements obtains a different one of the eight electrical interference signal values with the eight electrical interference signal values obtained simultaneously to compute the conjugated quadratures of fields of scattered/reflected orthogonally polarized fields. Each of the eight electrical interference signal values contains only information relevant to one orthogonal component of one of the two conjugated quadratures.

The bi- and quad-homodyne detection methods obtain measurements of electrical interference signals wherein each measured value of an electrical interference signal contains simultaneously information about two orthogonal components of conjugated quadratures. The two orthogonal components correspond to orthogonal components of conjugated quadratures such as described in cited U.S. Provisional Patent Application No. 60/442,858 (ZI-47) and cited U.S. patent application Ser. No. 10/765,369, filed Jan. 27, 2004 (ZI-47) entitled "Apparatus and Method for Joint Measurements of Conjugated Quadratures of Fields of Reflected/Scattered and Transmitted Beams by an Object in Interferometry".

The variants of the bi- and quad-homodyne detection methods obtain measurements of electrical interference signals wherein each measured value of an electrical interference signal contains simultaneously information about two orthogonal components of each of two conjugated quadratures of fields of scattered/reflected orthogonally polarized beams. The two orthogonal components of the two conjugated quadratures correspond to orthogonal components of conjugated quadratures such as described in cited U.S. Provisional Patent Application No. 60/459,425 (ZI-50) and cited U.S. Patent Application filed Apr. 1, 2004 (ZI-50) and entitled "Apparatus and Method for Joint Measurement of Fields of Scattered/Reflected Orthogonally Polarized Beams by an Object in Interferometry".

Figure 1B:
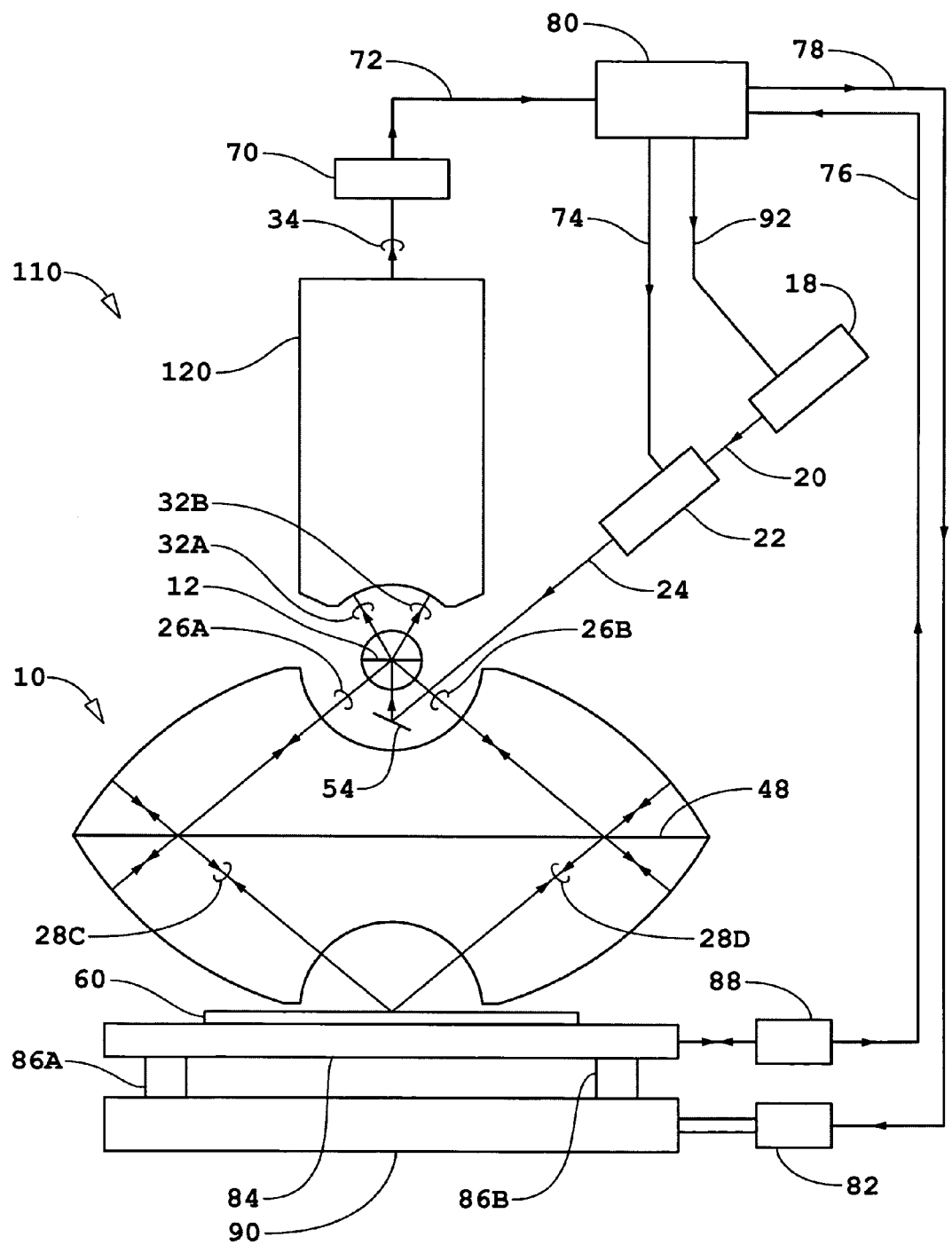
FIG. 1b is a schematic diagram of a confocal microscope system.

A first embodiment is shown schematically in FIG. 1b. The first embodiment comprises a first imaging system generally indicated as numeral 10, pinhole array beam-splitter 12, detector 70, and a second imaging system generally indicated as numeral 110. The second imaging system 110 is low power microscope having a large working distance, e.g. Nikon ELWD and SLWD objectives and Olympus LWD, ULWD, and ELWD objectives.

Figure 1C:
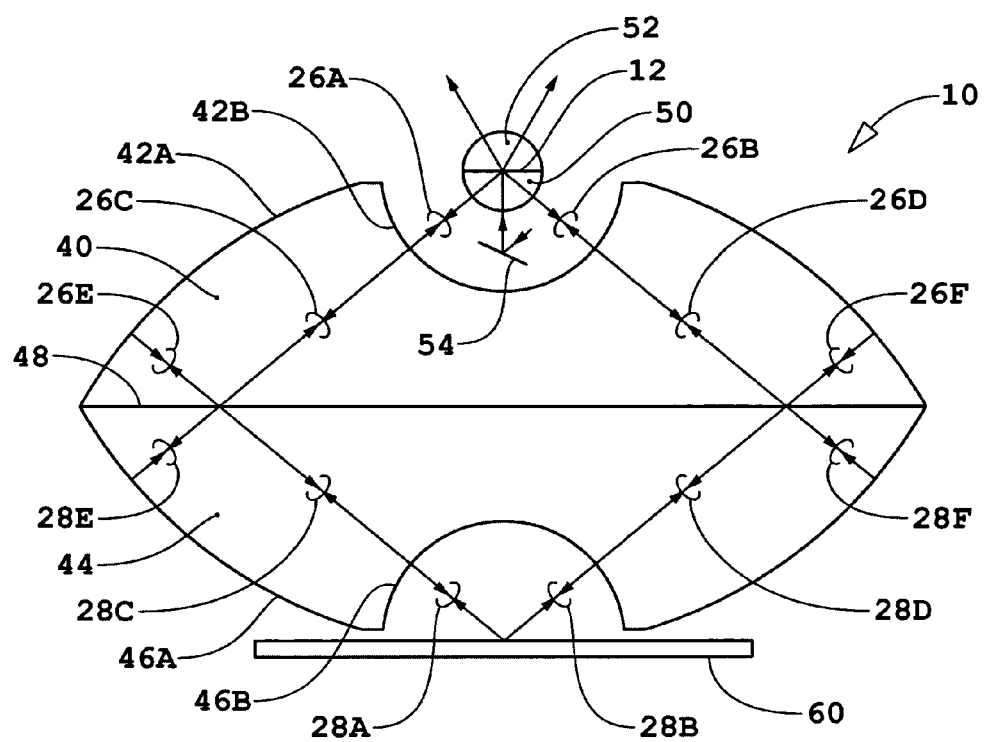
FIG. 1c is a schematic diagram of catadioptric imaging system.

The first imaging system 10 is shown schematically in FIG. 1c. The imaging system 10 is a catadioptric system such as described in commonly owned U.S. patent application Ser. No. 10/028,508 (ZI-38) and U.S. Pat. No. 6,717,736 (ZI-43) both of which are entitled "Catoptric and Catadioptric Imaging System." Both of the two cited patent applications are by Henry A. Hill and the contents of the two cited patent applications are incorporated herein in their entirety by reference.

Catadioptric imaging system 10 comprises catadioptric elements 40 and 44, beam-splitter 48, and convex lens 50. Surfaces 42A and 46A are convex spherical surfaces with nominally the same radii of curvature and the respective centers of curvature of surfaces 42A and 46A are conjugate points with respect to beam-splitter 48. Surfaces 42B and 46B are concave spherical surfaces with nominally the same radii of curvature. The centers of curvature of surfaces 42B and 46B are the same as the centers of curvature of surfaces 46A and 42A, respectively. The center of curvature of convex lens 50 is the same as the center of curvature of surfaces 42B and 46A. The radius of curvature of surface 46B is selected so as to minimize the loss in efficiency of the imaging system 10 and to produce a working distance for imaging system 10 acceptable for an end use application. The radius of curvature of convex lens 50 is selected so that the off-axis aberrations of the catadioptric imaging system 10 are compensated. The medium of elements 40 and 44 may be for example $CaF_2$, fused silica or commercially available glass such as SF11. The medium of convex lens 50 may be for example $CaF_2$, fused silica, YAG, or commercially available glass such as SF11. An important consideration in the selection of the medium of elements 40 and 44 and convex lens 50 will the transmission properties for the frequencies of beam 24.

Figure 1D:
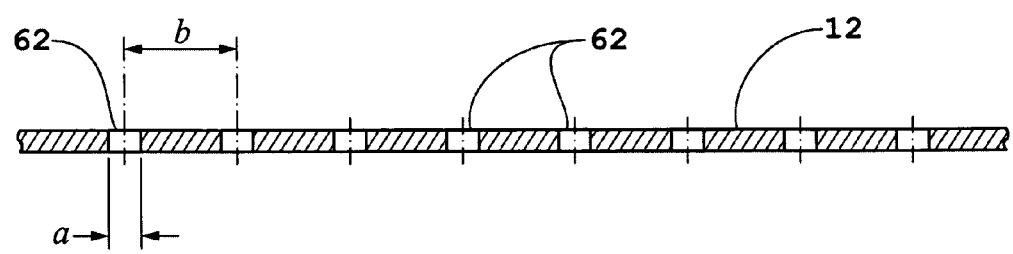
FIG. 1d is a schematic diagram of a pinhole array used in a confocal microscope system.

Convex lens 52 has a center of curvature the same as the center of curvature of convex lens 50. Convex lenses 50 and 52 are bonded together with pinhole beam-splitter 12 in between. Pinhole array beam-splitter 12 is shown in FIG. 1d. The pattern of pinholes in pinhole array beam-splitter is chosen to match the requirements of an end use application. An example of a pattern is a two dimensional array of equally spaced pinholes in two orthogonal directions. The pinholes may comprise circular apertures, rectangular apertures, or combinations thereof such as described in commonly owned U.S. patent application Ser. No. 09/917,402 (ZI-15) entitled "Multiple-Source Arrays for Confocal and Near-field Microscopy" by Henry A. Hill and Kyle Ferrio of which the contents thereof are incorporated herein in their entirety by reference. The pinholes may also comprise microgratings such as described in cited U.S. Provisional Patent Application No. 60/459,425 (ZI-50) and U.S. Patent Application filed Apr. 1, 2004 (ZI-50) and entitled "Joint Measurement Of Fields Of Orthogonally Polarized Beams Scattered/Reflected By An Object In Interferometry". A nonlimiting example of a pinhole array for pinhole array beam-splitter 12 is shown in FIG. 1d having a spacing between pinholes of b with aperture size a.

The description of the imaging properties of catadioptric imaging system 10 is the same as the corresponding portion of the description given for the imaging properties of catadioptric imaging system 10 in commonly owned U.S. Provisional Patent Application No. 60/442,982 (ZI-45) entitled "Interferometric Confocal Microscopy Incorporating Pinhole Array Beam-Splitter" and U.S. patent application Ser. No. 10/765,229, filed Jan. 27, 2004 (ZI-45) and also entitled "Interferometric Confocal Microscopy Incorporating Pinhole Array Beam-Splitter" both of which are by Henry A. Hill. The contents of both of the U.S. Provisional Patent Application and the U.S. Patent Application are herein incorporated in their entirety by reference.

Input beam 24 is reflected by mirror 54 to pinhole beam-splitter 12 where a first portion thereof is transmitted as reference beam components of output beam components 32A and 32B (see FIG. 1b) and a second portion thereof scattered as measurement beam components of beam components 26A and 26B. The measurement beam components of beam components 26A and 26B are imaged as components of beam components 28A and 28B to an array of image spots in an image plane close to the surface of substrate 60. A portion of the components of beam components 28A and 28B incident on substrate 60 are reflected and/or scattered as return measurement beam components of beam components 28A and 28B. Return measurement beam components of beam components 28A and 28B are imaged by catadioptric imaging system 10 to spots that are coincident with the pinholes of pinhole beam-splitter 12 and a portion thereof is transmitted as return measurement beam components of output beam components 32A and 32B.

The next step is the imaging of output beam components 32A and 32B by imaging system 110 to an array of spots that coincide with the pixels of a multi-pixel detector such as a CCD to generate an array of electrical interference signals 72. The array of electrical interference signals is transmitted to signal processor and controller 80 for subsequent processing.

Conjugated quadratures of fields of the return measurement beam are obtained in embodiments by one of the single-, double-, bi-, and quad-homodyne detection methods and variants thereof. For the homodyne detection methods, a set of measurements of electrical interference signals 72 is made. For each of the sets of measurements of the electrical interference signals 72, known phase shifts are introduced between the reference beam components and respective return measurement beam components of output beam components 32A and 32B. A non-limiting example of a known set of phase shifts for the single-homodyne detection method comprise 0, $\pi/4$, $\pi/2$, and $3\pi/2$ radians, mod $2\pi$.

In practice, the known phase shifts introduced between the reference beam components and respective measurement beam components of output beam components 32A and 32B are generated by two different techniques. In one technique, phase shifts are introduced between the reference beam components and the respective measurement beam components for each of the frequency components of beam 24 by source 18 and beam-conditioner 22 as controlled by signals 92 and 74, respectively, from electronic processor and controller 80. In the second technique, phase shifts are introduced between the reference and measurement beam components for each of the frequency components as a consequence of frequency shifts introduced to the frequency components of input beam 24 by source 18 and beam-conditioner 22 as controlled by signals 92 and 74, respectively, from electronic processor and controller 80.

With respect to the second technique, an optical path difference L is introduced between the reference beam components and the respective return measurement beam components of output beam components 32A and 32B. As a consequence, there will be for a frequency shift $\Delta f$ a corresponding phase shift $\phi$ where $$\varphi = 2\pi L\left(\frac{\Delta f}{c}\right) \quad (1)$$

and c is the free space speed of light. Note that L is not a physical path length difference and depends for example on the average index of refraction of the measurement beam and the return measurement beam paths. For an example of a phase shift $\phi=\pi$, $3\pi$, $5\pi$, . . . and a value of L=0.25 m, the corresponding frequency shift $\Delta f$=600 MHz, 1.8 GHz, 3.0 GHz, . . . .

Two different modes of operation are described for the acquisition of the four or eight electrical interference signal values. The first mode to be described is a step and stare mode wherein substrate 60 is stepped between fixed locations for which image information is desired. The second mode is a scanning mode. In the step and stare mode for generating a one-, a two-, or a three-dimensional image of substrate 60, substrate 60 is translated by stage 90 wherein substrate 60 is mounted on wafer chuck 84 with wafer chuck 84 mounted on stage 90. The position of stage 90 is controlled by transducer 82 according to servo control signal 78 from electronic processor and controller 80. The position of stage 90 is measured by metrology system 88 and position information acquired by metrology system 88 is transmitted to electronic processor and controller 80 to generate an error signal for use in the position control of stage 90. Metrology system 88 may comprise for example linear displacement and angular displacement interferometers and cap gauges.

Electronic processor and controller 80 translates stage 90 to a desired position and then acquires the set of four or eight electrical interference signal values. After the acquisition of the sequence of four or eight electrical interference signal values, electronic processor and controller 80 then repeats the procedure for the next desired position of stage 90. The elevation and angular orientation of substrate 60 is controlled by transducers 86A and 86B.

The second of the two modes for the acquisition of the electrical interference signal values is next described wherein the electrical interference signal values are obtained with the position of stage 90 scanned in one or more directions. In the scanning mode, source 18 is pulsed at times controlled by signal 92 from signal processor and controller 80. Source 18 is pulsed at times corresponding to the registration of the conjugate image of pinholes of pinhole array beam-splitter 12 with positions on and/or in substrate 60 for which image information is desired.

There will be a restriction on the duration or "pulse width" of a beam pulse $\tau_{p1}$ produced by source 18 as a result of the continuous scanning used in the scanning mode of the first embodiment unless pinhole array 12 is scanned to track the conjugate image of substrate 60 at pinhole array 12 such as described in cited U.S. Provisional Patent Application No. 60/442,982 (ZI-45) and U.S. patent application Ser. No. 10/765,229, filed Jan. 27, 2004 (ZI-45) and entitled "Interferometric Confocal Microscopy Incorporating Pinhole Array Beam-Splitter". Pulse width $\tau_{p1}$ will be a parameter that in part controls the limiting value for spatial resolution in the direction of a scan to a lower bound of $$\tau_{p1}V, \quad (2)$$

where V the scan speed. For example, with a value of $\tau_{p1}$=50 nsec and a scan speed of V=0.20 m/sec, the limiting value of the spatial resolution $\tau_{p1}V$ in the direction of scan will be $$\tau_{p1}V=10 \text{ nm}. \quad (3)$$

Pulse width $\tau_{p1}$ will also determine the minimum frequency difference that can be used in the bi- and quad-homodyne detection methods and variants thereof. In order that no contributions to the electrical interference signals are generated from interference between fields of conjugated quadratures, the minimum frequency spacing $\Delta f_{min}$ is expressed as $$\Delta f_{min} \gg \frac{1}{\tau_{p1}}. \quad (4)$$

For an example of $\tau_{p1}$=50 nsec, $1/\tau_{p1}$=20 MHz.

In the first mode, i.e., the step and stare mode, each set of the sets of arrays of electrical interference signal values corresponding to the set of phase shift values are generated by a single pixel of detector 70 for single- and bi-homodyne detection methods and variants thereof, by two pixels of detector 70 for the quad-homodyne detection method and variant thereof, by four pixels of detector 70 for the double-homodyne detection method, and by eight pixels of detector 70 for the variant of the double-homodyne detection method. In the second mode for the acquisition of the electrical interference signal values, each corresponding set of electrical interference signal values are generated by a conjugate set of different pixels of detector 70 for each of the four homodyne detection methods and variants thereof. Thus in the first mode of acquisition, the differences in pixel efficiency are compensated in the signal processing by signal processor and controller 80 for the double-, bi-, and quad-homodyne detection methods and in variants of the bi- and quad-homodyne detection methods. In the second mode of acquisition, the differences in pixel efficiency and the differences in sizes of pinholes in pinhole array beam-splitter 12 need to be compensated in the signal processing by electronic processor and controller 80 to obtain conjugated quadratures of fields of return measurement beam components.

The advantage of the second mode is that the electrical interference signal values are acquired in a scanning mode which increases throughput of the interferometric confocal and non-confocal microscopy systems.

The processing of the measured arrays of sets of measured electrical interference signal values for the determination of conjugated quadratures of fields of return measurement beams is described in cited references. With respect to the bi- and quad-homodyne detection methods wherein conjugated quadratures are obtained jointly, a set of four electrical interference signal values is obtained for each spot on and/or in substrate 60 being imaged. The processing of the measured arrays of sets of measured electrical interference signal values for the determination of conjugated quadratures of fields of return measurement beams is described for example in cited U.S. Provisional Patent Application No. 60/442,858 (ZI-47) and cited U.S. patent application Ser. No. 10/765,369, filed Jan. 27, 2004 (ZI-47) and entitled "Apparatus and Method for Joint Measurements of Conjugated Quadratures of Fields of Reflected/Scattered and Transmitted Beams by an Object in Interferometry".

With respect to the variants of the bi- and quad-homodyne detection methods wherein conjugated quadratures are obtained jointly, a set of eight electrical interference signal values is obtained for each spot on and/or in substrate 60 being imaged. The processing of the measured arrays of sets of measured electrical interference signal values for the determination of conjugated quadratures of fields of return measurement beams is described for example in cited U.S. Provisional Patent Application No. 60/459,425, filed Apr. 1, 2003 (ZI-50) and cited U.S. patent application Ser. No. 10/816,180 filed Apr. 1, 2004 and entitled "Apparatus and Method for Joint Measurement of Fields of Scattered/Reflected Orthogonally Polarized Beams by an Object in Interferometry", both of which are incorporated herein by reference.

In the embodiment, multi-pixel detector 70 may comprise a frame transfer CCD that is configured such that one set of CCD pixel signal values may be generated and subsequently stored on the CCD wafer while a frame of a second set of CCD pixel signal values may be generated before a readout of both the first and second set of the CCD signal values is made. The time required to store the first set of CCD signal values is generally much less than the time required to readout a set of CCD signal values for a frame transfer CCD. Thus, the advantage of the use of a frame transfer CCD is that the time between two consecutive pulses of input beam 20 and the corresponding time between measurements of electrical interference signal values can be much less than when using a non-frame transfer CCD.

The first embodiment is configured for non-ellipsometric non-joint measurement of conjugated quadratures of fields of beams scattered/reflected at the spots in or on substrate 60. In the first embodiment, input beam 24 comprises one frequency component wherein non-joint measurements of conjugated quadratures are obtained using the single homodyne detection method. The phase shifts between the reference beam components and the respective return beam components of output beam components 32A and 32B are generated in the first embodiment by shifting the frequency of the input beam 24 between known frequency values. There is a difference in optical path length between the reference beam components and the respective return beam components of output beam components 32A and 32B and as a consequence, a change in frequency of input beam 24 will generate a corresponding phase shift between the reference beam components and the respective return beam components of output beam components 32A and 32B.

A second embodiment is described that is configured for non-ellipsometric joint measurement of conjugated quadratures of fields of beams scattered/reflected at the spots in or on substrate 60. The second embodiment comprises the interferometric confocal microscopy system of the first embodiment operated for joint measurement of conjugated quadratures using the bi-homodyne detection method. In the second embodiment, beam-conditioner 22 is operated to generate beam 24 comprising two frequency-shifted components.

The remaining description of the second embodiment is the same as corresponding portions of the description given of the first embodiment.

Figure 1E:
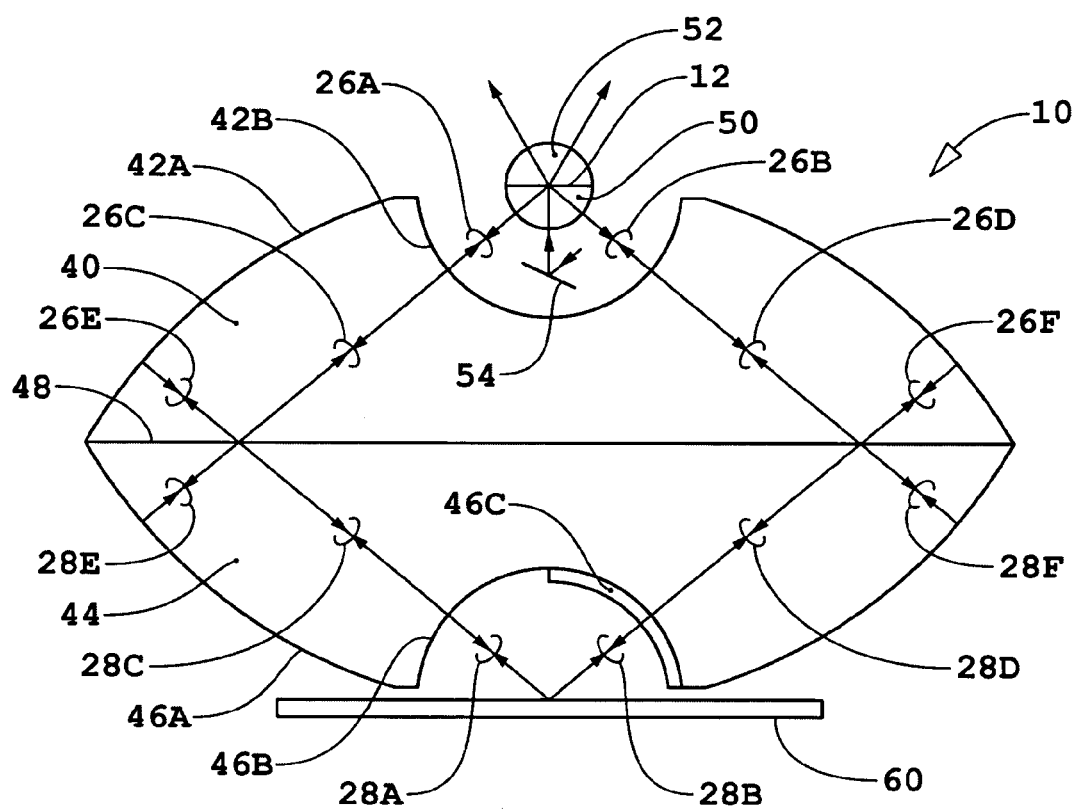
FIG. 1e is a schematic diagram of catadioptric imaging system with a phase shifter.

The sum of the forward scattered/reflected components and the backscattered components of return measurement beam components of beam components 26A and 26B are measured in the first or second embodiments by making a first non-joint or joint measurement, respectively, of the conjugated quadratures of fields of measurement beams scattered/reflected at the spots in or on substrate 60 as described. Next a $\pi/2$ phase shifter is introduced either at concave surface 42B or at concave surface 46B for either the right half or left half of the aperture of the imaging system 10 shown in FIG. 1c. An example of a $\pi/2$ phase shifter 46C is shown in FIG. 1e in the right half of the aperture of imaging system 10 at concave surface 46B. With $\pi/2$ phase shifter 46C in place, the forward scattered/reflected components and the backscattered components of return measurement beam components of beams 26A and 26B are next measured in the first or second embodiments, respectively, by making a second non-joint or joint measurement, respectively, of the conjugated quadratures of fields of measurement beams scattered/reflected at the spots in or on substrate 60.

The relative phase of the reference and return measurement beam components of beams 32A and 32B are the same in both of the first and second set of non-joint or joint measurements of the conjugated quadratures of fields of measurement beams scattered/reflected at the spots in or on substrate 60 for the forward scattered/reflected components. However, as a consequence of the $\pi/2$ phase shift introduced by the $\pi/2$ phase shifter 46C, the relative phase of the backscattered components of return measurement beam components of beams 32A and 32B are different by $\pi$ and as a result interferometrically cancel out in the second set of non-joint or joint measurements, respectively, of the conjugated quadratures of fields of measurement beams scattered/ reflected at the spots in or on substrate 60. As a consequence of the effect of $\pi/2$ phase shifter 46C, only the forward scattered/reflected component of the fields scattered/reflected by the spots on or in substrate 60 is obtained from the second set of non-joint or joint measurements, respectively, of the conjugated quadratures of fields. Accordingly the backscattered component of the fields scattered/reflected by the spots on or in substrate 60 is obtained by subtracting the second set of non-joint or joint measurements, respectively, of the conjugated quadratures of fields from the first set of non-joint or joint measurements, respectively, of the conjugated quadratures of fields.

The measurement of the backscattered component of the fields scattered/reflected by the spots on or in substrate 60 permits for example the measurement of critical dimensions of arrays of trenches with sub-wavelength trench widths. Also the number of trenches in an array of trenches that have a total width less than the lateral resolution of imaging system 10 can be determined. The backscattering measurement feature is particularly valuable in the measurement of properties of trenches because of the constructive interference properties of the backscattered fields from an array of trenches functioning as a grating of a finite number of rulings.

A third embodiment is described that comprises the interferometric confocal microscopy system of the first embodiment operated for joint measurement of conjugated quadratures of fields of beams scattered/reflected at the spots in or on substrate 60 using the quad-homodyne detection method. In the third embodiment, source 18 and beam-conditioner 22 are operated to generate beam 24 comprising four frequency-shifted components. The remaining description of the third embodiment is the same as corresponding portions of the description given of the first embodiment.

A fourth embodiment is described that comprises the interferometric confocal microscopy system of the first embodiment operated for non-joint measurement of conjugated quadratures of fields of beams scattered/reflected at the spots in or on substrate 60 using the double-homodyne detection method. In the fourth embodiment, source 18 and beam-conditioner 22 are operated to generate beam 24 comprising four frequency-shifted components. The remaining description of the fourth embodiment is the same as corresponding portions of the description given of the first embodiment.

In other embodiments, the first, second, third, and fourth embodiments are configured to make ellipsometric non-joint and joint measurements of fields of scattered/reflected orthogonally polarized beams by the spots on or in substrate 60. The first, second, third, and fourth embodiments use variants of the single-, double-, bi-, and quad-homodyne detection methods such as described in cited U.S. Provisional Patent Application No. 60/459,425 (ZI-50] and U.S. Patent Application No. 10/816,180 filed Apr. 1, 2004 entitled "Apparatus and Method for Joint Measurement Of Fields Of Scattered/Reflected Orthogonally Polarized Beams By An Object In Interferometry". In the other embodiments, pinhole array 12 may be replaced by an array of microgratings such as described in cited U.S. Provisional Patent Application No. 60/459,425 (ZI-50] and U.S. Patent Application No. 10/816,180 filed Apr. 1, 2004 entitled "Apparatus and Method for Joint Measurement Of Fields Of Scattered/Reflected Orthogonally Polarized Beams By An Object In Interferometry".

The information obtained in the other embodiments are of the ellipsometric type and furnish additional information with respect to the behavior of the backscattered fields with respect to state of polarization of the measurement beam at the spot in or on substrate 60.

In embodiments, pinhole array beam-splitter 12 may be scanned in a direction opposite to the direction of scan of substrate 60 and with a speed such that the conjugate images of the pinholes of pinhole array beam-splitter 12 stay superimposed with spots on or in substrate 60 that are being imaged. This scanning mode of operation reduces the restriction on the pulse width $\tau_{p1}$ and is analogous to the relative motions of reticle stage and a wafer stage of a lithography tool operating in a scanning mode. The issue of traditional critical alignment of conjugate confocal pinholes in a confocal microscopy system is non-existent, i.e. the registration of the pinholes generating the array of reference beams and the pinholes generating the array of measurement beams is automatic.

In certain end use applications, the interior of substrate 60 is imaged. In this case, there will be aberrations introduced. In another embodiment, compensation for aberrations is accomplished by introducing a thin layer (the thin layer has an index of refraction different from lens 50) between lens 50 and pinhole array beam-splitter 12 such as described in commonly owned U.S. Provisional Application No. 60/444,707 (ZI-44) entitled "Compensation of Effects of Mismatch in Indices of Refraction At a Substrate-Medium Interface in Confocal and Interferometric Confocal Microscopy" and U.S. patent application Ser. No. 10/771,785, filed Feb. 4, 2004 (ZI-44) and also entitled "Compensation for Effects of Mismatch in Indices of Refraction at a Substrate-Medium Interface in Confocal and Interferometric Confocal Microscopy" both of which are by Henry A. Hill. The contents of the U.S. Provisional Patent Application and the U.S. Patent Application are incorporated herein in their entirety by reference.

For certain other embodiments, phase shifts are introduced in interferometer 10 of FIG. 1a that serve the function of the $\pi/2$ phase shifter 46C of the cited embodiments, i.e., the first, second, third, and fourth embodiments and other embodiments. In each of the certain other embodiments, there is an imaging system for imaging substrate 60 onto a pinhole array and/or multi-pixel detector array and an imaging system for imaging a source onto substrate 60. These two imaging systems may comprise the same imaging system such as for the cited embodiments. In the certain other embodiments, the two imaging systems may be two independent imaging systems or have common portions thereof. In each embodiment of the certain embodiments, the function of the $\pi/2$ phase shifter 46C of the cited embodiments, wherein the two imaging systems are the same, is achieved in interferometer 10 of FIG. 1a by the introduction of a $\pi/2$ phase shifter in one half of the aperture of the stop for each of the two imaging systems. (Note: In general, an imaging system is characterized by an aperture stop that defines an aperture or opening through which the light that forms the image will pass. That is, the aperture stop limits the cross-section of light that will form the image.) The relative orientations of the two phase shifters are such that any component of a measurement beam that reaches the detector as a component that is forward scattered/reflected by substrate 60 will a pass through either one of the two $\pi/2$ phase shifters, but not both as it traverses from the source to the detector. On the other hand, any component of a measurement beam that reaches the detector as a component that is backscattered by substrate 60 will either pass through both phase shifters or neither phase shifter as it traverses from the source to the detector. In the cases where the two imaging systems share a common portions thereof, the role of the two π/2 phase shifters that cover one half of the apertures of the stops for each of the two imaging systems may be achieved by a single π/2 phase shifter, such as in the case of the cited embodiments.

A fifth embodiment comprises the interferometer system of FIG. 1a with interferometer 10 comprising an interferometric far-field confocal microscope such as described in commonly owned U.S. Pat. No. 5,760,901 entitled "Method And Apparatus For Confocal Interference Microscopy With Background Amplitude Reduction and Compensation" by Henry A. Hill, the contents of which are herein incorporated in their entirety by reference. In the fifth embodiment, source 18 and beam-conditioner 22 are configured to operate in a phase shifting mode. The fifth embodiment has reduced effects of background because of background reduction features of cited U.S. Pat. No. 5,760,901.

A sixth embodiment comprises the interferometer system of FIG. 1a with interferometer 10 comprising an interferometric far-field confocal microscope such as described in cited U.S. Pat. No. 5,760,901 wherein the phase masks are removed. In the sixth embodiment, source 18 and beam-conditioner 22 are configured to operate in a phase shifting mode. The sixth embodiment with the phase masks of embodiments of cited U.S. Pat. No. 5,760,901 removed represent applications of confocal techniques in a basic form.

A seventh embodiment comprises the interferometer system of FIG. 1a with interferometer 10 comprising an interferometric far-field confocal microscope such as described in commonly owned U.S. Pat. No. 6,480,285 B1 entitled "Multiple Layer Confocal Interference Microscopy Using Wavenumber Domain Reflectometry and Background Amplitude Reduction and Compensation" by Henry A. Hill, the contents of which are herein incorporated in their entirety by reference. In the seventh embodiment, source 18 and beam-conditioner 22 are configured to operate in a phase shifting mode. The seventh embodiment has reduced effects of background because of background reduction features of cited U.S. Pat. No. 6,480,285 B1.

An eighth embodiment comprises the interferometer system of FIG. 1a with interferometer 10 comprising an interferometric far-field confocal microscope such as described in cited U.S. Pat. No. 6,480,285 B1 wherein the phase masks are removed. In the eighth embodiment, source 18 and beam-conditioner 22 are configured to operate in a phase shifting mode. The eighth embodiment with the phase masks of embodiments of cited U.S. Pat. No. 6,480,285 B1 removed represent applications of confocal techniques in a basic form.

A ninth embodiment comprises the interferometer system of FIG. 1a with interferometer 10 comprising an interferometric near-field confocal microscope such as described in commonly owned U.S. Pat. No. 6,445,453 (ZI-14) entitled "Scanning Interferometric Near-Field Confocal Microscopy" by Henry A. Hill, the contents of which are herein incorporated in their entirety by reference. In the ninth embodiment, source 18 and beam-conditioner 22 are configured to operate in a phase shifting mode. The eighth embodiment of cited U.S. Pat. No. 6,445,453 in particular is configured to operate in a mode with the measurement beam separated from the reference beam and incident on the substrate being imaged by a non-confocal imaging system, i.e., the measurement beam at the substrate is not an image of an array of pinholes but an extended spot. Accordingly, the corresponding embodiments of the ninth embodiment represent a non-confocal configuration for the measurement beam in both non-ellipsometric and ellipsometric measurements.

Other embodiments are within the following claims.

What is claimed is:

1. An interferometry system for making interferometric measurements of an object, said system comprising:
    a source assembly that generates an input beam;
    a detector assembly that includes a detector element; and
    an interferometer that includes a source imaging system that focuses the input beam onto a spot on or in the object and an object imaging system that images the spot onto the detector element as an interference beam, said object imaging system combining light coming from the spot with a reference beam to produce the interference beam,
    wherein the source imaging system is characterized by a first aperture stop that defines a first aperture, said source imaging system including a first phase shifter that introduces a first phase shift in light passing through a first region of the first aperture relative to light passing through a second region of the first aperture, said second region of the first aperture being the region of the aperture that is outside of the first region of the first aperture, and
    wherein the object imaging system is characterized by a second aperture stop that defines a second aperture, said object imaging system including a second phase shifter that introduces a second phase shift in light passing through a first region of the second aperture relative to light passing through a second region of the second aperture, said second region of the second aperture being the region of the aperture that is outside of the first region of the second aperture.

2. The interferometry system of claim 1, wherein the first and second phase shifters are oriented relative to each other such that any component of the input beam that reaches the detector element as a result of being forward scattered/reflected by the object passes through only one of the first and second phase shifters when traversing from the source assembly to the detector element.

3. The interferometry system of claim 1, wherein the first and second phase shifters are oriented relative to each other such that any component of the input beam that reaches the detector element as a result of being backscattered by the object passes through either both the first and second phase shifters or through neither of the first and second phase shifters when traversing from the source assembly to the detector element.

4. The interferometry system of claim 2 wherein the first phase shift is π/2 and the second phase shift is π/2.

5. The interferometry system of claim 2, wherein the first region of the first aperture occupies one half of the area of the first aperture and wherein the first region of the second aperture occupies one half of the area of the second aperture.

6. The interferometry system of claim 2, wherein the first and second regions of the first aperture are of equal area.

7. The interferometry system of claim 2, wherein the first and second regions of the second aperture are of equal area.

8. The interferometry system of claim 2, wherein the object imaging system includes a first imaging system, a mask defining a pinhole, and a second imaging system, wherein the first imaging system images the spot on the pinhole of the mask and the second imaging system images the pinhole of the mask onto the detector element.

9. The interferometry system of claim 8, wherein the second phase shifter is located in the first imaging system.

10. The interferometry system of claim 2, wherein the object imaging system includes a first imaging system and a mask defining a pinhole, and wherein the first imaging system and the source imaging system are both implemented by the same imaging system.

11. The interferometry system of claim 10, wherein the object imaging system also includes a second imaging system that images the pinhole onto the detector element.

12. The interferometry system of claim 10, wherein the first phase shifter is a thin optical film on a portion of a surface of an optical element within the source imaging system.

13. The interferometry system of claim 12, wherein the second phase shifter is also implemented by said thin film.

14. The interferometry system of claim 10, wherein the interferometer comprises a catadioptric imaging system that implements both the source imaging system and the first imaging system.

15. The interferometry system of claim 14, wherein the catadioptric imaging system comprises a first catadioptric element, a second catadioptric element, and a beam splitter between the first and second catadioptric elements.

16. The interferometry system of claim 2, wherein the interferometry system is an interferometric microscopy system.

17. The interferometry system of claim 2, wherein the interferometry system is a interferometric confocal microscopy system.

18. The interferometry system of claim 2, wherein the interferometry system is an interferometric ellipsometric microscopy system.

19. The interferometry system of claim 2, wherein the source assembly comprises a pulsed or shuttered source for generating the input beam.

20. An interferometry system for making interferometric measurements of an object, said system comprising:
a source assembly that generates an array of input beams;
a detector assembly that includes an array of detector elements; and
an interferometer that includes a source imaging system that focuses the array of input beams onto an array of spots on or in the object and an object imaging system that images the array of spots onto the array of detector elements as an array of interference beams, said object imaging system combining light coming from each spot of the array of spots with a corresponding reference beam to produce a corresponding interference beam of the array of interference beams,
wherein the source imaging system is characterized by a first aperture stop that defines a first aperture, said source imaging system including a first phase shifter that introduces a first phase shift in light passing through a first region of the first aperture relative to light passing through a second region of the first aperture, said second region of the first aperture being the region of the first aperture that is outside of the first region of the first aperture, and
wherein the object imaging system is characterized by a second aperture stop that defines a second aperture, said object imaging system including a second phase shifter that introduces a second phase shift in light passing through a first region of the second aperture relative to light passing through a second region of the second aperture, said second region of the second aperture being the region of the second aperture that is outside of the first region of the second aperture.

21. The interferometry system of claim 20, wherein the first and second phase shifters are oriented relative to each other such that any component of the array of input beams that reaches the detector element as a result of being forward scattered/reflected by the object passes through only one of the first and second phase shifters when traversing from the source assembly to the detector element.

22. The interferometry system of claim 21, wherein the first and second phase shifters are oriented relative to each other such that any component of the array of input beams that reaches the detector element as a result of being backscattered by the object passes through either both of the first and second phase shifters or through neither of the first and second phase shifters when traversing from the source assembly to the detector assembly.

23. The interferometry system of claim 21, wherein the first phase shift is $\pi/2$ and the second phase shift is $\pi/2$.

24. The interferometry system of claim 21, wherein the first region of the first aperture occupies one half of the area of first aperture and wherein the first region of the second aperture occupies one half of the area of the second aperture.

25. The interferometry system of claim 21, wherein the first and second regions of the first aperture are of equal area.

26. The interferometry system of claim 21, wherein the first and second regions of the second aperture are of equal area.

27. The interferometry system of claim 21, wherein the first phase shifter is a thin optical film on a portion of a surface of an optical element within the source imaging system.

28. The interferometry system of claim 27, wherein the second phase shifter is also implemented by said thin film.

29. The interferometry system of claim 21, wherein the object imaging system includes a first imaging system, a detector-side mask defining an array of pinholes, and a second imaging system, wherein the first imaging system images the array of spots on the array of pinholes so that each imaged spot of the imaged array of spots is aligned with a corresponding different one of the pinholes of the array of pinholes and wherein the second imaging system images the array of pinholes onto the array of detector elements.

30. The interferometry system of claim 29, wherein the interferometer comprises a catadioptric imaging system that implements both the source imaging system and the first imaging system.

31. The interferometry system of claim 30, wherein the catadioptric imaging system comprises a first catadioptric element, a second catadioptric element, and a beam splitter between the first and second catadioptric elements.

32. The interferometry system of claim 30, wherein the source assembly includes a source-side mask defining an array of pinholes.

33. The interferometry system of claim 32, wherein the detector-side mask and the source-side mask are implemented by the same mask.

34. The interferometry system of claim 21, wherein the source assembly comprises a pulsed source for generating the array of input beams.

35. The interferometry system of claim 29 further comprising an object stage for holding the object.

36. The interferometry system of claim 35 further comprising a first transducer assembly for moving the object stage so as to scan the object during operation.

37. The interferometry system of claim 36 further comprising a second transducer assembly for moving the detector-side mask during operation.

38. The interferometry system of claim 37 further comprising a controller programmed to cause the first transducer to move the object while at the same time causing the second transducer assembly to move the detector-side mask so that the detector-side mask tracks a conjugate image of the object during operation.

39. A method of making interferometric measurements of an object, said method comprising:
  generating a input beam;
  deriving first and second measurement beams from the input beam;
  focusing the first and second measurement beams onto a spot on or in the object to produce a first return measurement beam and a second return measurement beam, said first return measurement beam resulting from forward reflection and/or forward scattering of the first measurement beam by the object plus backscattering of the second measurement beam by the object, said second measurement beam resulting from forward reflection and/or forward scattering of the second measurement beam by the object plus backscattering of the first measurement beam by the object;
  interfering the first and second return measurement beams with a reference beam to produce an interference beam;
  focusing the interference beam onto the detector element to produce an interference signal; and
  establishing measurement conditions by shifting the first measurement beam in phase relative to the second measurement beam by a first amount and by shifting the second return measurement beam in phase relative to the first return measurement beam by a second amount.

40. The method of claim 39, wherein the first and second amounts of phase shift are such that the backscattering portions of the first and second return measurement beams substantially cancel and the forward reflected and/or forward scattering portions of the first and second return measurement beams reinforce each other.

41. The method of claim 39, wherein the first and second amounts of phase shift are equal.

42. The method of claim 41, wherein the first and second amounts of phase shift are both equal to $\pi/2$.

43. The method of claim 39, further comprising, under the established measurement conditions, measuring the interference signal to produce first results.

44. The method of claim 43, further comprising establishing other measurement conditions by refraining from shifting the first measurement beam in phase relative to the second measurement beam and by refraining from shifting the second return measurement beam in phase relative to the first return measurement beam.

45. The method of claim 44, further comprising, under the other established measurement conditions, measuring the interference signal to produce second results.

46. The method of claim 45, further comprising using the first and second results to compute a backscattered component from the object.

47. The method of claim 46, wherein using the first and second results comprises subtracting the first results from the second results to compute the backscattered component from the object.

* * * * *